United States Patent [19]

Kimble

[11] Patent Number: 4,641,669

[45] Date of Patent: Feb. 10, 1987

[54] METHOD FOR REINFORCING AND HARDENING HUMAN NAILS

[76] Inventor: Lorraine Kimble, P.O. Box 32, 8962 E. Hampden Ave., Denver, Colo. 80231

[21] Appl. No.: 724,930

[22] Filed: Apr. 19, 1985

[51] Int. Cl.$^4$ ............................................. A45D 29/00
[52] U.S. Cl. ..................................................... 132/73
[58] Field of Search ........................ 132/73, 73.5, 88.5, 132/88.7

[56] References Cited

U.S. PATENT DOCUMENTS

| | | | |
|---|---|---|---|
| 4,007,748 | 2/1977 | Matranga et al. | 132/73 |
| 4,157,095 | 6/1979 | Sweet | 132/73 |
| 4,267,852 | 5/1981 | Hullinger | 132/73 |
| 4,299,243 | 11/1981 | Umstattd | 132/73 |
| 4,361,160 | 11/1982 | Bryce | 132/73 |
| 4,407,310 | 10/1983 | Jadow | 132/73 |
| 4,552,160 | 11/1985 | Griggs | 132/73 |

*Primary Examiner*—Hugh R. Chamblee
*Attorney, Agent, or Firm*—Charles C. Corbin

[57] ABSTRACT

A method for repairing, reinforcing, and hardening natural human nails.

11 Claims, No Drawings

METHOD FOR REINFORCING AND HARDENING HUMAN NAILS

BACKGROUND

It is well known that for various reasons the human nails, particularly women's nails, often exhibit a tendency to become brittle, to show surface unevenness, or to crack and split.

Various methods have been made available in an attempt to prevent and/or remedy these various nail imperfections. One known method involves the use of liquid compositions called "nail hardeners" which are topically applied to the nail and dry and harden to form a protective coating. Examples are described in U.S. Pat. No. 4,381,294 and U.S. Pat. No. 4,260,701. Another nail hardening method is shown in U.S. Pat. No. 4,407,310 in which a layer of a suitable nail glue is applied to the nail and a granular material is deposited on the film of glue to form a textured protective surface.

Unfortunately while the above-described prior art methods and other known techniques do show nail hardening capabilities, they nevertheless do not provide the strength, structural integrity and durability yet flexibility that is achievable with the present invention.

SUMMARY OF THE INVENTION

In view of the foregoing, it is an objective of the present invention to provide a new method for preserving the finger nail and to prevent it from chipping, splitting and breaking.

Another objective is to provide a method for mending damaged nails.

A further objective is to provide a nail hardening method that gives a nail coating that has high strength and durability qualities, yet which is flexible.

Accordingly, the present invention provides a nail treating process which includes applying to the natural nail surface a patch comprising of a thin mat of natural cellulose fibers followed by saturation of the in-place patch with a cyanoacyrlate glue. The individual fibers are thereby bonded to one another and to the nail surface. Thus, the flexibility yet high strength and structural integrity inherent in a bonded fiber mat is provided in a novel and non-obvious way to form a protective nail coating.

DETAILED DESCRIPTION OF THE INVENTION

To practice the method of the invention, the user prepares the finger nail by cleaning it and pushing the cuticle back with a manicure stick. From a thin mat of non-heat sealed random cellulose fibers, such as may be formed of hemp and other natural cellulose fibers, a piece is cut that generally conforms to the configuration of the nail. The fiber mat best suited to the invention has a thickness ranging from 0.040 mm to 0.050 mm, fiber diameters in the range of 10.7 microns to 26.7 microns and surface density from 1.10 mg/cm$^2$ to 1.34 mg/cm$^2$, preferably 1.22 mg/cm$^2$. The patch is placed upon the nail surface and aligned therewith. A cyanoacrylate glue, preferably ethyl alpha cyanoacrylate, is applied to the patch in sufficient quantity to cover it. The glue will permeate the fiber patch and also engage the nail surface and rapidly cure to create bonds of fiber-to-fiber and fiber-to-nail. The steps of applying fiber patch and glue is preferably repeated three times.

The resulting coating is given an initial sanding with an intermediate grade of emery board. A fine grade emery paper, preferably on a cushioned emery tool of conventional design in the cosmetic industry, is then used to provide a final smooth finish. A drop of mineral oil applied to the finished coating will then impart to it a natural appearance.

What is claimed is:

1. Method for reinforcing human nails comprising the steps of:
   a. cutting from a thin mat of natural cellulose fibers a patch of said mat that generally conforms to the shape of the nail and placing said patch on the surface of the nail;
   b. applying a coat of a bonding composition to said patch sufficient to permeate the patch and bond intersecting fibers to one another and to the nail surface;
   c. allowing said bonding composition to dry;
   d. repeating steps a. and b. for a plurality of times; and
   e. shaping and smoothing the resulting bonded fiber coat.

2. Method according to claim 1 wherein steps b and c are repeated three times.

3. Method according to claim 1 wherein said mat has a surface density in the range of 1.10 mg/cm$^2$ to 1.34 mg/cm$^2$.

4. Method according to claim 1 wherein said mat has a surface density of 1.2 mg/cm$^2$.

5. Method according to claim 1 wherein said bonding composition is a cyanoacrylate glue.

6. Method according to claim 5 wherein said glue is ethyl alpha cyanoacrylate.

7. Method according to claim 1 including a final step of applying a coating of mineral oil.

8. Method according to claim 1 wherein said mat is composed of hemp fibers.

9. Method according to claim 1 wherein said mat has a thickness in the range of 0.040 mm to 0.050 mm.

10. Method according to claim 9 including fibers having diameters in the range of 10.7 microns to 26.7 microns.

11. Method according to claim 10 wherein said mat has a surface density in the range of 1.10 mg/cm$^2$ to 1.34 mg/cm$^2$.

* * * * *